United States Patent [19]
Zdeblick et al.

[11] Patent Number: 5,324,290
[45] Date of Patent: Jun. 28, 1994

[54] ANTERIOR THORACOLUMBAR PLATE

[75] Inventors: Thomas A. Zdeblick, Madison, Wis.; Michael C. Sherman, Memphis, Tenn.

[73] Assignee: Danek Medical, Inc., Memphis, Tenn.

[21] Appl. No.: 949,910

[22] Filed: Sep. 24, 1992

[51] Int. Cl.$^5$ ............................................. A61B 17/56
[52] U.S. Cl. ...................................... 606/61; 606/69
[58] Field of Search .................. 623/16, 17; 606/61, 606/60, 65, 66, 67, 68, 69, 70

[56] References Cited

U.S. PATENT DOCUMENTS

| | | | |
|---|---|---|---|
| 4,503,848 | 3/1985 | Caspar et al. | 606/69 |
| 4,696,290 | 9/1987 | Steffee | 606/69 |
| 4,800,874 | 1/1989 | David et al. | 606/69 |
| 4,867,144 | 9/1989 | Karas et al. | 606/89 |
| 5,015,248 | 5/1991 | Burstein et al. | 606/69 |
| 5,147,361 | 9/1992 | Ojima et al. | 606/69 |

Primary Examiner—David Isabella
Attorney, Agent, or Firm—Woodard, Emhardt, Naughton Moriarty & McNett

[57] ABSTRACT

An internal anterior fixation system for treatment of vertebral burst fractures includes an elongated plate having longitudinal axis which includes integral superior, inferior and bridge portions. The superior and inferior portions are provided for fixation to corresponding vertebrae while the bridge portion spanning between the portions over the affected vertebra. The superior portion includes a pair of generally parallel elongated slots therethrough each having scallops on for receiving bone fixation screws or bolts. The inferior portion includes a pair of openings through which fixation screws or bolts extend. The slots in the superior portion allow for compression or distraction of the intermediate vertebral region. The openings in the inferior portion are oriented at an oblique angle relative to the axis of the plate to provide a quadrilateral fixation construct. The bridge portion has a width significantly less than the width of the superior and inferior fixation portions.

9 Claims, 2 Drawing Sheets

ANTERIOR THORACOLUMBAR PLATE

BACKGROUND OF THE INVENTION

The present invention concerns devices for the anterior fixation of the spine. In particular, the present invention relates to a plate for the fixation of thoracic or lumbar vertebra. The plate of the present invention has particular application in situations where vertebral body corpectomies are performed, such as burst fractures with significant spinal canal compromise or vertebral body tumors.

Fractures of the spine commonly occur at the thoracolumbar junction, and particular in the T-11, T-12, L-1 or L-2 vertebrae. In the past, treatment of burst fractures involved prolonged bed rest in a body cast and/or a brace. Harrington rods were the first widely successful devices implementing internal fixation for treatment of a vertebral burst fracture. The Harrington rods involved posterior distraction of the spine and allowed some reduction and restoration of vertebral height by means of distraction. However, the inability of Harrington rods to reduce a kyphosis or to clear the spinal canal completely were major disadvantages of this approach.

To improve reduction, posterior distraction systems were modified with the use of contoured rods, sleeves for the rods, improved hooks and sublaminar wires. However, with these posterior distraction systems, it was usually recommended that the spinal fusion include 2 vertebral levels caudad to the fracture and 2 or 3 levels cephalad to the fracture. The posterior approach, even to this level of advancement, was still less than an optimum solution to the problem of treatment of thoracolumbar burst fractures.

In the early 1980's an anterior approach was developed for treatment of burst fractures. Improved scanning techniques allowed visualization of bone fragments that were present with burst fractures, so that attention could then be directed toward complete decompression of the canal as a way to provide the best environment for neurological recovery. Various fixation devices have been developed since that time based upon this theory of internal anterior treatment of burst fractures. However, the anterior approach has in some cases lead to increased operative morbidity due to the very difficult nature of the procedure. In addition risk to the vascular network as well as complete clearance of the spinal canal has been a problem with many of the anterior fixation approaches. Most of the prior internal anterior systems suffer from a great degree of complexity.

One such system is the Kanada device marketed by Acromed, Inc. of Cleveland, Ohio. The Kanada device utilizes vertebral body staples through which fixation screws are placed into the vertebral body. Rods are then engaged between the screws in the superior and inferior vertebral bodies. Normally two screws are placed in each body, therefore requiring two rods between the vertebrae. The rods are threaded at their ends to allow compression and distraction.

Another device marketed by Zimmer, provides an anterior spinal fixation system indicated for treatment of tumors or thoracolumbar burst fractures. This device is described in the patent to Dunn, U.S. Pat. No. 4,289,123, which issued on Sep. 15, 1981. This device is similar to the Kanada device in that it uses rods between the superior and inferior vertebrae. A pair of large plates contoured to the vertebrae are engaged by way of a number of screws.

Several plating systems have been developed for anterior internal fixation of the spine. One of these plates, the Syracuse I-plate provides a number of differently sized I-shaped plates which are engaged across the burst fracture. However, the Syracuse I-plate does not allow for compression or distraction of a bone graft between the superior and inferior vertebrae.

Acromed Inc. markets a contoured anterior spinal fixation plate (CASF TM plate) which is indicated for treatment of lumbar burst fractures and tumors. The plate includes a number of screw openings through the contoured plate. The number of openings simply provide different locations for engaging a bone screw to the vertebra, and does not lend itself to compression or distraction of a bone graft. Duma International of Taipai, Taiwan, offers the Stafix plating system which includes a plate that has a number of screw holes and a single screw slot. The Stafix plate permits quadrilateral placement of bone screws, but is not readily adapted for compression or distraction. Moreover, this plate, as with the aforementioned anterior plates, lack the ability to provide rigid or semi-rigid fixation using bone screws or bone bolts.

Even with these prior anterior internal fixation systems, there remains a need for a plate and screw system for the efficient management of thoracolumbar burst fractures and tumors. There is a need for such a system which permits anterior load sharing, as well as compression and distraction. The system must also be easy to implant, to thereby reduce operative morbidity.

DESCRIPTION OF THE PREFERRED EMBODIMENTS

Figure 1:
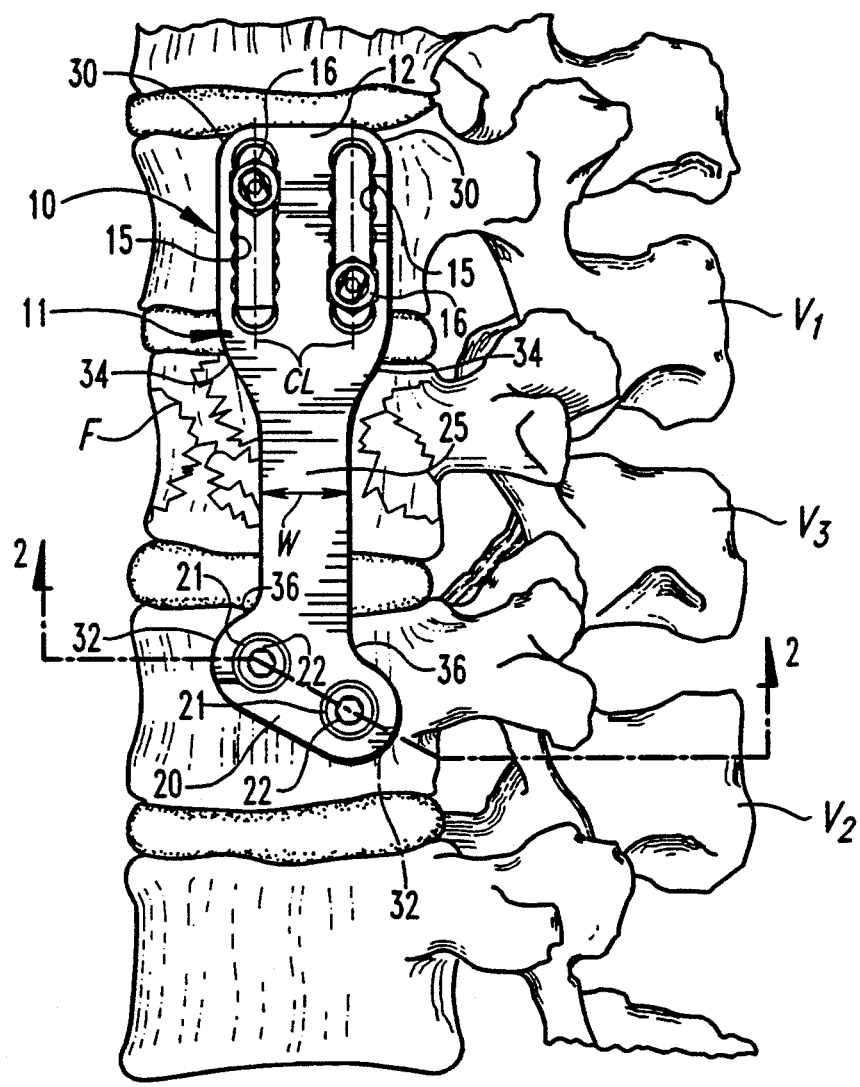
FIG. 1 is a side elevational view of an internal anterior thoracolumbar plate according to the present invention affixed between superior and inferior vertebrae about a burst fracture.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring first to FIG. 1, an anterior thoracolumbar plate system 10 in accordance with the present invention is illustrated. The system 10 includes a specially configured plate 11 engaged between superior vertebrae $V_1$ and inferior vertebra $V_2$. The plate 11 spans a vertebra $V_3$ having a burst fracture F. The vertebra $V_3$ can have been subjected to a vertebral body corpectomy, such as for a tumor resection. Alternatively, the present invention has application in situations where a vertebral bone graft spans between the inferior and superior vertebrae.

The plate 11 includes three distinct portions. The first portion, the superior portion 12, includes a pair of slots 15 formed therein. Each of the slots 15 is configured to receive a bone fixation element 16 therethrough. At the opposite end of the plate, the inferior portion 20 includes openings 21 therethrough to also receive a fixation element, such as a bone bolt or bone screw, for engagement with vertebra $V_2$. The superior and inferior portions 12 and 20, respectively, are interconnected by a bridge portion 25 which portion is configured to span the burst fracture vertebra $V_3$. As shown by a comparison of the plates shown in FIGS. 1 and 3, the distance between the superior and inferior portions 12 and 20 can be changed by modifying the length of the bridge portion 25.

It is understood that this bridge portion 25 can be lengthened or shortened depending upon the total length of the plate 11 required for the particular vertebral anatomy. The plate must be long enough for the fixation portions 12 and 20 to find sufficient solid purchase on the respective superior and inferior vertebrae. The overall length of the thoracolumbar plate of the present invention can be provided in half inch increments between 2.5 inches and 5.0 inches, depending upon the spinal anatomy and the number of vertebrae to be spanned by the plate.

The particular configuration of the anterior thoracolumbar plate 11 of the present invention is an important feature of the invention. For instance, all of the corners of the plate are rounded. Specifically, the corners 30 of the superior portion 12 and the ends 32 of the inferior portion 20 are rounded. In addition, the transition 34 between the superior portion 12 and bridge portion 25 is smoothly contoured, as is the transition 36 between the inferior portion 20 and the bridge 25. This "rounded" profile of the plate 11 reduces the trauma to surrounding tissue when the plate is implanted.

In another important aspect, the transverse width of the bridge portion 25 is smaller than the width of the fixation portions 12 and 20 of the plate 11. Unlike prior anterior plates, the plate 11 of the present invention limits the wider plate portions to those portions that directly interface the vertebrae. It has been found that the reduced profile of the bridge portion facilitates the plate's insertion and minimizes trauma to surrounding tissue, without sacrificing the ability of the plate to maintain stable fixation of the region. Preferably, the width W of the bridge portion 25 is slightly larger than the distance between the centerlines CL of the two slots 16 in the superior portion 12 of the plate. In one specific embodiment, this width is 0.5 inches.

Figure 2:
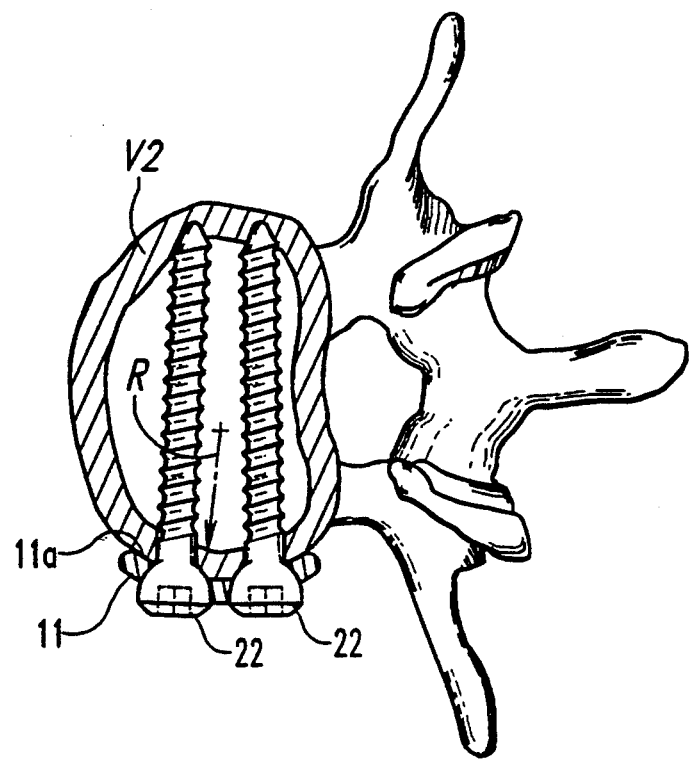
FIG. 2 is a cross sectional view of one end of the anterior thoracolumbar plate shown in FIG. 1, taken along line 2—2 as viewed in the direction of the arrows.

To facilitate fixation of the plate 11 to the vertebrae, the underside 11$b$ of the plate 11 is curved to match the outer curvature of the vertebral body of the vertebra $V_2$, as shown in FIG. 2. The underside of the plate is curved at a radius R, which in one specific embodiment can range between 1.0 and 1.5 inches depending upon the anatomy of the vertebrae to which the plate is affixed.

Figure 3:
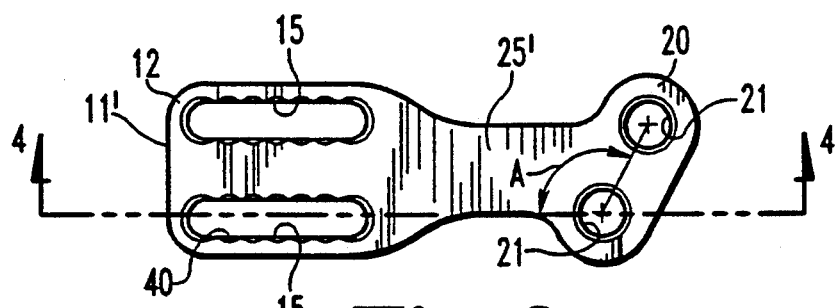
FIG. 3 is a top elevational view of an anterior thoracolumbar plate similar to the plate shown in FIG. 1 but having a shorter length.
Figure 4:
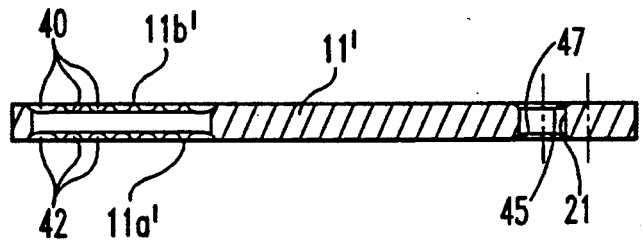
FIG. 4 is a side cross sectional view of the plate shown in FIG. 3, taken along line 4—4 as viewed in the direction of the arrows, particularly illustrating the scalloped configuration of the plate slots and screw openings.

Referring now to FIG. 3, additional important features of the anterior fixation plate of the present invention are shown. The plate 11' illustrated in FIG. 3 is identical to the plate 11 shown in FIG. 1, with the exception that the bridge portion 25' is shorter than the bridge portion 25 of the prior plate. As shown in FIG. 3, the plate 11' includes the pair of parallel elongated slots 15 through which fixation elements 16 can be engaged. Each of the slots includes an upper surface 11$b'$ defining a number of scallops 40 at the slot. In addition and alternatively, a number of scallops 42 can also be formed at the underside 11$a'$ of the plate.

The scallops 40 and 42 are adapted to receive rounded mating surfaces on bone screws or bone bolts, such as the bone screw 22 shown in FIG. 2. Bone fixation elements having contoured plate engagement surfaces are well known in the art to those or ordinary skill. A bone screw satisfying these requirements is the low profile bone screw sold by Danek Medical, Inc. as its part number series 803-370 thru 803-384. It is understood that a bone bolt can also be utilized which includes a contoured upper face to engage the scallops 42 at the underside 11$a'$ of the plate 11 prime. Such a bone bolt includes a lower threaded portion for engaging the vertebra, an intermediate portion for engaging the underside scallops 42, and an upper threaded portion which extends through the plate opening. A nut also having a contoured face is threaded onto the upper threaded portion of the bone bolt and tightened down onto the top surface 11$b'$ of the plate to clamp the plate to the bone bolt. A suitable bone bolt arrangement is disclosed in the patent to Heinig et al., U.S. Pat. No. 4,887,595, and in U.S. Pat. No. 5,129,899 to Small et al. Either of the bone screws or bone bolts preferably include a hex drive recess to permit "top-loading" and tightening of the fixation elements.

In one important aspect of the anterior plate of the present invention, the slots 15 and openings 21 allow fixation of the plate to the vertebrae using either bone screws or bone bolts, or a combination of both. Which of the bone screws or bone bolts is used depends upon the degree of fixation required. Use of bone screws, such as screws 22, tends to provide a less rigid fixation than that provided by dual-threaded bone bolts in which the bolt intermediate portion contacts the underside 11$a'$ of the plate 11'. The nature of the burst fracture F tends to dictate the degree of fixation required in the procedure. This flexibility in fixation approach has not been available in prior internal anterior fixation devices.

As can be seen from FIGS. 1 and 3, the elongated slots 15 extend along an axis parallel to the longitudinal axis of the plate 11 and 11'. The length of the slots, as well as the presence of the scallops 40 and 42, allow compression and distraction to be performed after the bone screws 16 have been engaged into the vertebra. Thus, in a typical procedure, the plate can be installed with the bone screws 16 extending through the slots 15, but not tightened firmly into the vertebra. Once compression or distraction is accomplished the screws are tightened down onto the plate to clamp the plate to the vertebra, thereby forming a solid fixation. Moreover, the scalloped slots allow the screws to be repositioned postoperatively as required to maintain an appropriate degree of compression of distraction at the fracture or graft site. Repositioning the screws postoperatively inherently adjusts the distance between the superior and inferior vertebrae, a feature lacking in prior art devices. Closing the distance between the fixed vertebrae is essential to develop compression on a bone graft between the vertebrae.

At the other end of the plate, that is at inferior portion 20, a pair of openings 21 are provided. As with the elongated slots, the openings 21 can include an upper countersunk portion 45 and a lower countersunk portion 47 to receive contoured heads of bone screws or bone bolts therethrough. It can be seen that a line drawn through the centers of the two openings 21 is oriented at an oblique angle A to the longitudinal axis of the plates 11, 11'. This particular angular orientation provides for a stable, firm quadrilateral construct which in turn allows for optimum anterior load sharing between the connected vertebrae. As can be seen in FIG. 1, in a typical procedure the screws 16 in superior portion 12 are also engaged at an angle relative to the longitudinal axis of the plate to complete the quadrilateral construct.

The plates 11 and 11' are formed of a bio-compatible material, such as 316LVM stainless steel. Other materials are contemplated, such as titanium alloy, provided the material is bio-compatible and has the requisite stiffness for anterior fixation of the spine.

The interior anterior fixation system 10 of the present invention, and particularly the anterior plate 11, provides means for firm anterior fixation of the spine, particularly at the thoracolumbar junction. The plate 11 is configured to facilitate fusion of a minimal number of motion segments. The plate also provides means for adjustment of the fixation screws or bolts to permit compression or distraction. The profile of the plate reduces tissue trauma and facilitates implantation. The plate 11 of the present invention accomplishes all of these functions as well as providing a quadrilateral construct and varying degrees of fixation rigidity.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An internal anterior fixation system for treatment of vertebral burst fractures, comprising:

an elongated plate having a longitudinal axis and including a superior portion, an inferior portion and a bridge portion integrally spanning between said superior and inferior portions, said superior portion defining a pair of elongated slots therethrough each having a longitudinal slot axis generally parallel to said longitudinal axis of said plate and a constant width along said slot axis, said inferior portion defining a pair of openings therethrough each having a centroid and an axis through said centroid parallel to and offset from said longitudinal axis of said plate and relatively offset from each other; and vertebral fixation elements having a bone engaging portion and a plate engaging portion adapted to extend through either of said slots or said openings in said plate for engaging said plate.

2. The internal anterior fixation system of claim 1, wherein said centroid of each of said pair of openings in said inferior portion defines a line therebetween, said line defining an oblique angle relative to said longitudinal axis of said plate.

3. The internal anterior fixation system of claim 1, wherein said superior portion and said inferior portion each have a width, and said bridge portion has a width substantially less than the width of said superior and inferior portions.

4. The internal anterior fixation system of claim 1, wherein said pair of elongated slots are arranged such that the longitudinal slot axes of said slots are mutually parallel.

5. The internal anterior fixation system of claim 4, wherein said bridge portion has a width less than the width of either of said superior and said inferior portions, and substantially equal to the distance between the longitudinal slot axes of said slots.

6. The internal anterior fixation system of claim 1, wherein said plate includes a number of scallops defined in the upper surface of said plate about the perimeter of each of said elongated slots.

7. The internal anterior fixation system of claim 6, wherein said plate includes a number of scallops defined in the lower surface of said plate about the perimeter of each of said elongated slots.

8. The internal fixation system of claim 1, wherein said axis through said centroid of each of said pair of openings in said inferior portion is colinear with said longitudinal slot axis of a corresponding one of said elongated slots in said superior portion of said plate.

9. The internal fixation system of claim 1, wherein said plate includes a curved lower surface for contacting a vertebra defined at a curvature to conform to the curvature of an anterior surface of the vertebra.

* * * * *